United States Patent [19]

Eden

[11] 4,169,862
[45] Oct. 2, 1979

[54] LOW TEMPERATURE CATALYTIC COMBUSTION OF CHLOROHYDROCARBONS

[75] Inventor: Jamal S. Eden, Akron, Ohio

[73] Assignee: The B. F. Goodrich Company, Akron, Ohio

[21] Appl. No.: 490,391

[22] Filed: Jul. 22, 1974

[51] Int. Cl.$^2$ .............................................. C07C 21/00
[52] U.S. Cl. ............................ 260/654 A; 260/656 R; 260/659 A; 423/481
[58] Field of Search .......... 260/656 R, 654 A, 659 A; 423/481

[56] References Cited

U.S. PATENT DOCUMENTS

| | | | |
|---|---|---|---|
| 3,453,073 | 7/1969 | Sims | 423/481 |
| 3,879,481 | 4/1975 | Sze et al. | 260/656 R |
| 4,053,557 | 10/1977 | Kayeyama | 423/481 |

FOREIGN PATENT DOCUMENTS 1086222  10/1967  United Kingdom ................ 260/656 R

*Primary Examiner*—Delbert E. Gantz
*Assistant Examiner*—Joseph A. Boska
*Attorney, Agent, or Firm*—Roy P. Wymbs

[57] ABSTRACT

There is disclosed an improved method of making chlorinated derivatives of ethylene wherein chlorine-containing by-products are burned in a catalytic combustion reactor to produce primarily a hydrogen halide which is recycled to the chlorinated derivative reaction and the heat of combustion from said reactor is utilized to preheat the materials used in said chlorinated derivative reaction. The catalyst employed is one containing 0.01% to 0.50% of platinum or palladium on 99.99% to 99.50% $Al_2O_3$, $SiO_2$ or a combination of $Al_2O_3$ and $SiO_2$ as a support and having a surface area of at least 50 square meters per gram. The catalytic combustion reaction is carried out at temperatures in the range of about 300° C. to about 450° C. to produce a mixture of gases containing essentially hydrogen chloride and being substantially free of elemental chlorine and chlorohydrocarbon compounds, said gases being then mixed with ethylene and reacted to form ethylene dichloride (EDC).

14 Claims, No Drawings

LOW TEMPERATURE CATALYTIC COMBUSTION OF CHLOROHYDROCARBONS

BACKGROUND OF THE INVENTION

In general, the field to which the present invention relates is that of producing chlorinated derivatives of ethylene, such as vinyl and vinylidene halides, particularly vinyl chloride. Also closely connected therewith is the synthesis of chlorinated solvents from, ethylene, chlorine and/or hydrogen chloride. Among such solvents are the highly chlorinated ethylenes, such as perchloroethylene, which is made by a process in which ethylene and/or partially chlorinated ethanes are subjected to one or more steps of catalytic oxyhydrochlorination with hydrogen chloride and oxygen.

Vinyl chloride is prepared by various processes from ethylene, elemental chlorine, and/or hydrogen chloride in most all of which a cracking step is employed wherein ethylene dichloride is thermally cracked in the vapor phase under pressure to vinyl chloride and by-product hydrogen chloride. The latter is recovered by an oxyhydrochlorination step wherein the hydrogen chloride is reacted with additional ethylene and oxygen to produce dichloroethanes which in turn are recycled to the cracking step. In many processes, a direct chlorination step is also employed wherein ethylene and elemental chlorine are reacted in liquid phase to produce dichloroethanes which are then cracked to vinyl chloride.

In all of these known solvent and monomer processes, the desired direct chlorination, oxyhydrochlorination, and/or cracking steps are not 100% selective to the desired chlorohydrocarbon end product and, as a result, fairly large quantities of undesired chlorine-containing by-products are obtained as complex mixtures which range in composition from chloroform or ethyl chloride to trichloroethanes and trichloroethylenes, tetrachloroethanes, hexachloroethanes, hexachlorobutadiene, etc., as well as aromatic compounds. Obviously, these undesirable chlorine-containing by-products pose economic, as well as ecological, problems of disposal.

Therefore, it would be most desirable and beneficial to have a process for producing chlorinated derivatives of ethylene and chlorinated solvents from ethylene, chlorine and/or hydrogen chloride wherein the heat energy product is utilized in the process and the production of unwanted chlorinated hydrocarbon by-products is substantially eliminated, or the end result is insignificant, due to reutilization of the waste products in the process.

SUMMARY OF THE INVENTION

The above problems of prior processes can be overcome or substantially eliminated by the present process wherein the unwanted chlorohydrocarbon by-products are recovered for reuse in the form of hydrogen chloride essentially free of elemental chlorine and chlorohydrocarbon impurities and said hydrogen chloride is recycled to the process for making chlorinated derivatives of ethylene. In addition, the intrinsic heat energy values of the crude by-products are returned to the process to preheat raw material feeds and intermediate feeds in the said process. Specifically, the process of the instant invention comprises passing the unwanted chlorohydrocarbon containing waste products through a heated bed of a catalyst containing 0.01% to 0.50% of platinum or palladium on 99.99% to 99.50% $Al_2O_3$, $SiO_2$ or a combination of $Al_2O_3$ and $SiO_2$ as a support, which catalyst bed is either fixed or is fluidized by air whereby said waste products are converted to a stream of combustion gases containing essentially only carbon oxides, water, inert gases and hydrogen chloride.

DETAILED DESCRIPTION

As used herein, the terms "chlorinated ethylene derivatives" and "chlorinated ethylene synthesis" are generic terms which encompass the various processes and their products wherein ethylene is reacted with elemental chlorine and/or hydrogen chloride in one step or in a plurality of steps to produce a chloroethylene or chloroethane type compound, such as vinyl chloride, vinylidene chloride, ethyl chloride, 1,1-dichloroethane, 1,2-dichloroethane, the trichloroethanes, the trichloroethylenes, the tetrachloroethanes, perchloroethylene, and many others. Thus, chlorinated ethylene synthesis includes any of the steps of direct chlorination of ethylene or of chlorinated ethylene derivatives, oxyhydrochlorination of ethylene or of chlorinated-ethylene derivatives whereby ethylene, or a chlorinated derivative thereof, are converted to products of higher chlorine content, and the cracking (dehydrochlorination) or rearrangement of chlorinated-ethylene derivatives to produce chlorinated-ethylene derivatives of lower chlorine content.

In the practice of the present invention the industrial waste materials containing chlorohydrocarbons are passed into and through a catalyst bed which is comprised of 0.01% to 0.50% of platinum or palladium on 99.99% to 99.50% $Al_2O_3$ or $SiO_2$ or a combination of $Al_2O_3$ and $SiO_2$, as a support. The catalyst bed may be either fixed or it may be fluid, that is, fluidized by air. The catalyst bed is maintained at a temperature in the range of about 300° C. to about 450° C. The preferred temperature range is from about 350° C. to about 400° C. In the catalyst bed, the waste materials are burned and converted to a stream of combustion gases containing essentially only carbon oxides, water, inert gases, and most importantly, hydrogen chloride. The time of contact of the waste materials with the catalyst bed is about 10 seconds to about 50 seconds. The catalyst at the temperatures employed causes essentially complete combustion of the chlorohydrocarbons in the waste stream but limiting said combustion so as to leave the hydrogen atoms attached to the chlorine atoms of the hydrogen chloride. This enables the production of a gas stream containing practically no elemental chlorine. Elemental chlorine is undesirable and production thereof must be avoided as far as possible. As complete combustion as possible is also important since the presence of chlorohydrocarbons in the combustion gases also tends to increase by-product formation in the oxyhydrochlorination step.

In the preparation of the catalysts of the present invention, either chloroplatinic acid ($H_2PtCl_6$) or palladium chloride ($PdCl_2$) is dissolved in distilled water and the resultant solution is then added to the support, that is, either $Al_2O_3$, $SiO_2$ or a mixture of the two. The wet impregnated catalyst support is then dried over hot air and calcined for approximately 16 hours at a temperature of 540° C. Thereafter the catalyst is ready for use in the process.

The waste materials, after entering the catalyst bed, are volatilized and then clearly burned in the controlled manner herein described. Even direct injection of the liquid waste stream, which is often viscous and tarry and containing materials comprised of suspended carbon, does not impair the catalyst bed and when employing a fluid bed, does not impair the fluidization thereof. Feeding the waste materials to the catalyst bed may easily be accomplished utilizing standard equipment, such as gear pumps, mechanical displacement pumps, and the like. In view of the temperatures employed in the present process, as described above, there are many conventional materials that may be used to house the catalyst bed which are capable of withstanding the corrosive environment encountered therein.

The pressure employed in the bed of the combustion catalyst of the present invention is not critical. For example, the catalytic combustion reaction can be carried out at atmospheric pressure, particularly if the combustion gases are not fed directly to the oxyhydrochlorination step or reaction. When said gases are so fed, they will have to be prepressurized to the same pressure existing in the oxyhydrochlorination reactor, since the oxyhydrochlorination reaction is normally operated above atmospheric pressure. Accordingly, it is desirable to maintain the gases in the combustion bed at a pressure in the range of about 25 to 150 psig., and preferably in a range of from about 40 to about 100 psig. In most cases, the pressure should be maintained just slightly higher than the pressure maintained in the oxyhydrochlorination step in order to avoid the necessity of compressing the combustion gases. Of course, when one is running experiments testing the present catalytic combustion reaction utilizing a simulated waste stream, atmospheric pressure is satisfactory and convenient since it avoids the necessity of pressurized equipment.

The combustion catalysts useful in the practice of the present invention are those containing from about 0.01% to 0.50% by weight, based on the total weight of catalyst, of platinum or palladium and from about 99.99% to about 99.50% by weight of either $Al_2O_3$, $SiO_2$ or a mixture of $Al_2O_3$ and $SiO_2$. When such a mixture is employed, its content will be from 13% to 94% by weight of $Al_2O_3$ and from 6% to 87% by weight of $SiO_2$. Further, the catalysts employed herein must have a high surface area, namely, a surface area of at least 50 square meters per gram ($m^2$/gm). The most active catalysts of this type are those having a surface area in the range of from about 175 $m^2$/gm to about 600 $m^2$/gm. It has been found that the most useful combustion catalyst for the present process is one containing pores averaging in size in the range of 30 Å to 60 Å in diameter. The most preferred catalyst is one containing 0.05% platinum or palladium and 99.95% $Al_2O_3$ or $SiO_2$ and having a surface area in the range of from about 175 to about 550 $m^2$/gm.

The components of the catalysts used herein are readily available commercially. For example, when employing a fluid bed in particular, $Al_2O_3$ and $SiO_2$ are readily available with the randomly wide particle size distribution required for good fluidization, namely, with few, if any, particles finer than 20 microns or larger than about 200 microns in average diameter and having the largest proportion of their particles in the range of from about 40 to about 140 microns in average diameter. Very small particles, or "fines", having an average diameter below about 20 microns should be avoided since they are too readily lost from the reactor. Similarly, large particles having an average diameter greater than about 200 microns are to be avoided since they are too difficult to fluidize. It is apparent, due to the nature of the present process, that the catalytic material must not be friable and should be resistant to attrition to the maximum extent possible.

In the present process the corrosive effect in the catalytic combustion chamber or reactor is very mild. In view of this, normal heat exchange coils made of conventional materials and design are inserted in the catalyst bed where they serve either as steam generating coils or as preheating coils for the raw or intermediate materials feed streams in the process for making chlorinated derivatives of ethylene. Even in those cases in making chlorinated derivatives of ethylene where only about 3% to 8% of the initial ethylene feed is converted to by-products, the annual savings in heat energy is very appreciable. Also, since the instant process is operated at low temperatures, the resulting combustion gases can be fed directly to the oxyhydrochlorination reaction without interstage cooling.

As pointed out hereinbefore, the present process may be carried out with the catalyst in fluidized form and utilizing air as the fluidizing agent or gas. When employing such a fluid bed catalyst system, the air must be employed in a sufficient quantity and at a rate of flow not only to completely fluidize the catalyst bed but also, to furnish sufficient oxygen for the controlled combustion of the hydrocarbons of the waste or by-product stream. In order to insure complete combustion of the waste stream, it is necessary that at least two moles of oxygen per mole of carbon in the waste stream be supplied to the reaction. However, in order to insure proper oxygen supply to the fluidized catalytic bed, sufficient air is fed to the bed to supply from about 2.5 moles to about 10.0 moles of oxygen per mole of carbon in the waste stream. When air feed rates are employed which provide an excess of about 10.0 moles of oxygen per mole of carbon in the waste stream, reduced capacity and catalyst losses result and, more importantly, it increases the risk of oxidation of the hydrogen chloride to elemental chlorine which, as has previously been pointed out, is to be avoided. When the air feed rates are such that less than about 2.0 moles of oxygen per mole of carbon in the waste stream are provided, only about 80% to 85% of complete combustion results. The preferred air feed rates are such that about 2.5 moles to about 5.5 moles of oxygen are provided for each mole of carbon in the waste feed stream. The above recited air feed rates are likewise applicable when employing a fixed catalyst bed, although in some instances, some slight adjustment may be necessary or desirable to attain maximum performance.

Contact times of the waste materials or by-products and the catalyst in the reactor may vary considerably without too much effect on the efficiency of combustion. When using a fluid bed reactor, contact times between about 5 seconds and about 50 seconds are satisfactory, keeping in mind that only about one-half of the calculated contact time represents time that the gases are in actual contact with the bed. This is because for the remainder of the time, the gases are in the free space above the bed in the catalyst disengaging and cyclone separator portions of the reactor. Best results have been obtained when the contact time is in the range of about 10 to about 50 seconds. When employing a fixed catalyst bed reactor, the preferred contact time is in the range of about 5 to about 25 seconds.

As previously pointed out, the most important variables in the instant catalytic combustion process are the temperature of the reaction and the catalytic efficiency of the catalyst. For example, when the temperature of the reaction is below 300° C., complete combustion cannot be achieved in reasonable contact times. When the reaction temperature is above 450° C., the combustion reaction is too vigorous and as a result, a portion of the hydrogen chloride is oxidized to elemental chlorine which, of course, is detrimental and is to be avoided.

I have found that most metal chlorides and metal oxides, when used alone, have some catalytic effect in the combustion reaction but to varying degrees. The difficulty with most of these compounds when used alone is that they function as Deacon catalysts thus converting or rearranging at least a portion of the chlorine content of the waste materials to form new polychlorinated hydrocarbons some of which are more resistant to oxidation. When so using such metallic catalysts, the combustion gases generally contain appreciable amounts of polychlorinated and unsaturated by-products. On the other hand, the catalysts of this invention have the desired catalytic activity and combustion gases produced therewith contain very little, and under optimum conditions, essentially no elemental chlorine and essentially no chlorohydrocarbon materials. Further, the catalysts of this invention are inexpensive and rugged in respect of their resistance to attrition and to fouling by unburned carbon and by the trace metallic content of the waste by-product feed streams.

By-product streams separated in various fractionation steps in many chlorinated ethylene syntheses contain up to 1 to 2% by weight of iron chloride as impurities. In the catalyst bed of the present invention, iron chlorides, and the like, are oxidized to finely divided iron oxides the bulk of which are carried out of the catalyst bed by the combustion gases and collected in the cyclone separators. The small amount of iron oxides retained by the catalyst bed are without apparent harmful effect on the catalyst bed efficiency. Also, any small amount of iron oxides carried out of the combustion reactor by the combustion gases to the subsequent oxyhydrochlorination step do not affect the oxyhydrochlorination catalyst which is normally on an alumina support. The only adverse effect, if any, of employing the combustion gases produced by the instant invention in the oxyhydrochlorination step is a very small decrease in capacity due to increased loadings of inert gases, from the combustion gases, in the oxyhydrochlorination feed.

When operating the present process utilizing a fluid bed, the combustion reactor is first charged with the solid granular catalyst. Upon the introduction of air, or fluidization, the catalytic bed expands to nearly completely fill the internal volume of the reactor. The catalyst bed is so fluidized before the addition thereto of the waste by-product stream. In feeding the by-product stream to the reactor, it is delivered to the same at a position just slightly above the bottom air inlet. Preferably, the waste stream is delivered to the reactor through a water-cooled nozzle which prevents vaporization and/or charring of the materials prior to contact of the materials with the catalyst of the bed.

In order to more clearly define the present invention the following specific examples are given, it being understood, of course, that this is merely intended to be illustrative and not limitative. In the examples, all parts and percents are by weight unless otherwsie indicated.

EXAMPLE I

In this example, the catalyst employed contained 0.5% by weight of platinum and 99.5% by weight of $Al_2O_3$. The catalyst was charged to a fluid bed maintained at atmospheric pressure. A simulated chlorinated hydrocarbon mixture was prepared and fed to the reactor at the rate of 1.5 ml./hour. Likewise, air was fed to the reactor at a rate of 6.25 liters/hour thus fluidizing the catalyst bed. The feed rate of the mixture was fixed so as to give a contact time between the mixture and the catalyst of about 17 seconds. The oxygen to carbon (as $C_2$) ratio was 2.63 and the hydrogen to chlorine ratio was 1.64. The temperature in the reactor was adjusted to 405°±5° C. The data with respect to feed and conversion is given in the following table:

TABLE I

| Content of Chlorinated Hydrocarbon Mixture | Feed Wt. % | Conversion % |
| --- | --- | --- |
| Trans 1,2-dichloroethylene | 3.06 | 100 |
| 1,1-dichloroethane | 3.06 | 100 |
| Cis 1,2-dichloroethylene | 3.06 | 100 |
| $CHCl_3$ | 3.06 | 100 |
| Ethylene dichloride | 35.71 | 100 |
| 1,1,1-trichloroethane | 5.10 | 100 |
| Benzene | 3.06 | 100 |
| Carbon tetrachloride | 3.06 | 100 |
| 1,1,2-trichloroethylene | 2.04 | 100 |
| 1,1,2-trichloroethane | 25.51 | 100 |
| 1,4-dichlorobutane | 3.06 | 100 |
| Chlorobenzene | 3.06 | 100 |
| 1,1,2,2-tetrachloroethylene | 2.04 | 100 |
| 5-tetrachloroethane | 2.04 | 100 |
| 1-chlorobutane | 3.06 | 100 |

The only products produced were HCl, $CO_2$, $H_2O$ and traces of highly chlorinated materials. No elemental chlorine was produced and the catalyst did not lose any activity after 385 hours of continuous operation. The results are presented in the following table:

TABLE II

| Elapsed Time Hours | Temp. ° C. | Contact time Seconds | % Balance Carbon | % Balance HCl |
| --- | --- | --- | --- | --- |
| 20 | 405 ± 5 | 17.5 | 94.20 | 97.25 |
| 44 | " | " | 94.24 | 92.61 |
| 76 | " | " | 109.68 | 92.92 |
| 99 | " | " | 96.85 | 99.10 |
| 120 | " | " | 103.59 | 98.79 |
| 157 | " | " | 104.56 | 96.63 |
| 234 | " | " | 104.93 | 89.53 |
| 306 | " | " | 110.23 | 103.11 |
| 330 | " | " | 107.54 | 108.36 |
| 365 | " | " | 105.51 | 100.02 |
| 385 | " | " | 101.10 | 100.02 |

EXAMPLE II

In this example, the same feed as in Example I was employed with 100% conversion. The catalyst contained 0.125% by weight of platinum and 99.875% by weight of $Al_2O_3$. The catalyst was charged to a fluid bed maintained at atmospheric pressure. The chlorinated hydrocarbon mixture was fed to the reactor at a rate of 1.5 ml./hr. and air was fed at a rate of 6.1 liters/hr. The contact time between the mixture and the catalyst was 17.5 seconds. The oxygen to carbon ratio was 2.63 and the hydrogen to chlorine ratio was 1.64. The temperature in the reactor was 400° C. Here again the catalyst oxidized the mixture completely to HCl, CO, $CO_2$ and $H_2O$ with only traces of polychlorinated benzenes. No free chlorine was detected. After 205 hours of continuous operation, the carbon balance was 105.84% and the HCl balance was 105.82%.

Another run was made using a catalyst of 0.05% by weight of platinum supported on 6% by weight of $SiO_2$ and 94% by weight of $Al_2O_3$. Complete conversion of the chlorinated hydrocarbon mixture was obtained at 410° C. and 18–19 seconds contact time.

EXAMPLE III

Again in this example, the same feed or chlorinated hydrocarbon mixture as in Example I was employed with 100% conversion. The catalyst employed contained 0.125% by weight of palladium and 99.875% by weight of $Al_2O_3$ and was charged to a fluid bed maintained at atmospheric pressure. The mixture was fed to the reactor or fluid bed at a rate of 1.5 ml./hour and air was fed to the reactor at a rate of 80 liters/hour. The contact time was 16.6 seconds and the temperature was maintained at 405°±5° C. The hydrogen to chlorine ratio was 1.64 (sample taken after 358 hours).

Data with respect to this example is given in the following table.

TABLE III

| Elapsed Time Hours | $O_2/C_2$ | Percent $O_2$ Conversion | % Balance Carbon | HCl |
|---|---|---|---|---|
| 5 | 3.16 | 62.33 | 102.84 | 96.41 |
| 75 | 3.16 | 70.09 | 102.26 | 104.55 |
| 100 | 3.58 | 60.81 | 102.16 | 101.64 |
| 125 | 3.58 | 55.05 | 99.90 | 100.19 |
| 174 | 3.44 | 61.46 | 102.69 | 99.15 |
| 181 | 3.44 | 56.13 | 95.68 | 100.38 |
| 205 | 3.44 | 55.22 | 94.58 | 102.88 |
| 229 | 3.44 | 55.22 | 99.34 | 94.58 |
| 253 | 3.44 | 55.27 | 94.28 | 94.54 |
| 310 | 3.44 | 58.95 | 91.95 | 98.07 |
| 358 | 3.44 | 54.36 | 98.01 | 100.10 |

The palladium catalyst did not lose any activity after 382 hours of continued operation and no elemental chlorine was produced under the operating conditions. Even though the conversion was substantially complete, a trace of unconverted chlorinated materials was observed.

The oxygen balance was good indicating the reliability of the data.

The instant invention provides a new and improved method of disposing of undesirable chlorinated by-products normally obtained when producing chlorinated derivatives of ethylene, such as in the production of vinyl chloride. The present method goes even further in that the catalytic oxidation permits recovering the contained chlorine in the waste products as hydrogen chloride which is then useable in the oxyhydrochlorination step in the production of chlorinated derivatives of ethylene.

Heretofore, hydrogen chloride has been recovered from the undesirable chlorinated by-products by incineration employing methane as a fuel. However, this method is very costly and unreliable. Further, such a process is highly impractical since the cost of recovery is more than five times the market price of the hydrogen chloride. On the other hand the present process is economical in that no additional fuel is necessary thus substantially reducing the cost of recovery. Also, the new method is advantageous in that the temperatures employed permit heat exchange for generating steam or the heat energy produced can be utilized in preheating the feed streams in the production of chlorinated derivatives of ethylene. Another advantage of the instant process is the fact that substantially no elemental or free chlorine is produced thus resulting in only an insignificant amount of corrosion of equipment. Numerous other advantages of the present invention will be readily apparent to those skilled in the art.

While the present invention has been described in terms of its specific embodiments, certain modifications and equivalents will be apparent to those skilled in the art and are intended to be included within the scope of the present invention, which is to be limited only by the reasonable scope of the appended claims.

I claim:

1. In the process of producing chlorinated derivatives of ethylene which includes the step of oxyhydrochlorination whereby hydrogen chloride is reacted with oxygen and ethylene, the improvement which comprises separating in a stream from said process any unwanted chlorinated ethylene derivatives and other by-products, injecting said stream into a combustion catalyst bed comprised of 0.01% to 0.5% by weight of platinum or palladium and 99.99% to 99.50% by weight of a material selected from the group consisting of $Al_2O_3$, $SiO_2$ and a mixture of $Al_2O_3$ and $SiO_2$, injecting air into said bed along with said stream, maintaining said bed at a temperature in the range of about 300° C. to about 450° C. to produce a mixture of hot combustion gases containing essentially hydrogen chloride and being essentially free of both elemental chlorine and chlorohydrocarbon materials, and recycling said mixture of gases to said oxyhydrochlorination step.

2. A process as defined in claim 1 wherein said catalyst bed is maintained under a pressure in the range of 25 to 150 psig.

3. A process as defined in claim 1 wherein said combustion catalyst has a surface area of at least 50 square meters per gram.

4. A process as defined in claim 1 wherein said combustion catalyst bed is fluidized by the injection of said air thereinto.

5. A process as defined in claim 1 wherein said stream is in contact with said combustion catalyst bed for a period in the range of about 10 to about 50 seconds.

6. A process as defined in claim 1 wherein said combustion catalyst bed is comprised of 0.01% to 0.5% by weight of platinum and 99.99% to 99.50% by weight of $Al_2O_3$.

7. A process as defined in claim 1 wherein said combustion catalyst bed is comprised of 0.01% to 0.5% by weight of palladium and 99.99% to 99.50% by weight of $Al_2O_3$.

8. A process as defined in claim 1 wherein said combustion catalyst bed is comprised of 0.5% by weight of platinum and 99.5% by weight of $Al_2O_3$.

9. A process as defined in claim 1 wherein the heat energy produced in said combustion catalyst bed is employed to preheat the material feed streams in said process of producing chlorinated derivatives of ethylene.

10. A process as defined in claim 2 wherein said combustion catalyst has a surface area of at least 50 square meters per gram and said bed is fluidized by the injection of said air thereinto.

11. A process as defined in claim 10 wherein said stream is in contact with said combustion catalyst bed for a period in the range of about 10 to about 50 seconds.

12. A process as defined in claim 6 wherein said catalyst bed is maintained under a pressure in the range of 25 to 100 psig. and said combustion catalyst has a surface area of at least 50 square meters per gram.

13. A process as defined in claim 12 wherein said combustion catalyst bed is fluidized by the injection of said air thereinto and said stream is in contact with said combustion catalyst bed for a period in the range of about 10 to about 50 seconds.

14. A process as defined in claim 13 wherein the heat energy produced in said combustion catalyst bed is employed to preheat the material feed streams in said process of producing chlorinated derivatives of ethylene.

* * * * *